United States Patent
Zhang et al.

(10) Patent No.: US 12,357,836 B2
(45) Date of Patent: *Jul. 15, 2025

(54) USER INTERFACE FOR NEURAL SIGNAL AND BIOMARKER VISUALIZATION AND ASSESSMENT

(71) Applicant: Boston Scientific Neuromodulation Corporation, Valencia, CA (US)

(72) Inventors: Tianhe Zhang, Studio City, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 278 days.

This patent is subject to a terminal disclaimer.

(21) Appl. No.: 17/975,486

(22) Filed: Oct. 27, 2022

(65) Prior Publication Data
US 2024/0139525 A1    May 2, 2024

Related U.S. Application Data

(63) Continuation of application No. 16/990,691, filed on Aug. 11, 2020, now Pat. No. 11,504,539.
(Continued)

(51) Int. Cl.
*A61N 1/372* (2006.01)
*A61N 1/36* (2006.01)

(52) U.S. Cl.
CPC ..... *A61N 1/37247* (2013.01); *A61N 1/36135* (2013.01); *A61N 1/36139* (2013.01);
(Continued)

(58) Field of Classification Search
CPC ............ A61N 1/37247; A61N 1/36139; A61N 1/36167; A61N 1/36185; A61N 1/37241;
(Continued)

(56) References Cited

U.S. PATENT DOCUMENTS

2009/0157155 A1    6/2009 Bradley
2017/0303811 A1*  10/2017 Gharib ................ A61B 5/4041
(Continued)

OTHER PUBLICATIONS

"U.S. Appl. No. 16/990,691, Examiner Interview Summary mailed Jun. 29, 2022", 2 pgs.
(Continued)

*Primary Examiner* — Eugene T Wu
(74) *Attorney, Agent, or Firm* — Schwegman Lundberg & Woessner, P.A.

(57) ABSTRACT

An example of a neurostimulation system may include a storage device for storing data representing physiological signals and a user interface including a user input, a display screen, and a presentation control circuit. The user input may be configured to receive a selection of signal(s) from the physiological signals and a selection of viewing mode from viewing modes including a metric mode and/or a presence mode. The metric mode allows for visualization of a signal property indicated by a parameter measured from the selected signal(s). The presence mode allows for viewing presence of a feature in the selected signal(s). The presentation control circuit may be configured to allow for the selection of the signal(s) and the viewing mode, to determine a segment of each of the selected signal(s) for presentation according to the selected viewing mode, and to present the determined segment on the display screen.

20 Claims, 10 Drawing Sheets

Related U.S. Application Data

(60) Provisional application No. 62/887,314, filed on Aug. 15, 2019.

(52) U.S. Cl.
CPC ..... *A61N 1/36167* (2013.01); *A61N 1/36185* (2013.01); *A61N 1/37241* (2013.01)

(58) Field of Classification Search
CPC .............. A61N 1/0551; A61N 1/37217; A61N 1/36062
See application file for complete search history.

(56) References Cited

U.S. PATENT DOCUMENTS

| | | | |
|---|---|---|---|
| 2017/0361101 A1* | 12/2017 | Single | A61N 1/36071 |
| 2018/0267700 A1 | 9/2018 | Kaditz et al. | |
| 2019/0134382 A1* | 5/2019 | Agnesi | A61N 1/36062 |
| 2020/0305744 A1* | 10/2020 | Weerakoon | A61N 1/025 |
| 2021/0046322 A1 | 2/2021 | Zhang et al. | |

OTHER PUBLICATIONS

"U.S. Appl. No. 16/990,691, Non Final Office Action mailed Mar. 28, 2022", 8 pgs.
"U.S. Appl. No. 16/990,691, Notice of Allowance mailed Jul. 27, 2022", 7 pgs.
"U.S. Appl. No. 16/990,691, Response filed Jun. 23, 2022 to Non Final Office Action mailed Mar. 28, 2022", 15 pgs.

* cited by examiner

USER INTERFACE FOR NEURAL SIGNAL AND BIOMARKER VISUALIZATION AND ASSESSMENT

CLAIM OF PRIORITY

This application is a continuation of U.S. application Ser. No. 16/990,691, filed Aug. 11, 2020, which claims the benefit of priority under 35 U.S.C. § 119(e) of U.S. Provisional Patent Application Ser. No. 62/887,314, filed on Aug. 15, 2019, which is herein incorporated by reference in its entirety.

TECHNICAL FIELD

This document relates generally to neurostimulation and more particularly to a neurostimulation system that includes a user interface for user-selectable visualization and assessment of sensed neural signals and biomarkers.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical pulses. The delivery is controlled using stimulation parameters that specify spatial (where to stimulate), temporal (when to stimulate), and informational (patterns of pulses directing the nervous system to respond as desired) aspects of a pattern of the electrical pulses. Efficacy and efficiency of certain neurostimulation therapies can be improved, and their side-effects can be reduced, by determining these stimulation parameters based on a patient's conditions and therapeutic objectives. A process of determining the stimulation parameters may include evaluation of sensed physiological signals and biomarkers, including those resulting from controlling delivery of the neurostimulation energy using the stimulation parameters.

SUMMARY

An example (e.g., "Example 1") of a neurostimulation system for delivering neurostimulation pulses and analyzing responses to the delivery may include a storage device and a user interface. The storage device may be configured to store data representing physiological signals each sensed via a sensing channel of sensing channels. The user interface may include a user input, a display screen, and a presentation control circuit. The user input may be configured to receive a selection of one or more physiological signals from the physiological signals and a selection of viewing mode from viewing modes. The view modes may include at least one of a metric mode or a presence mode. The metric mode allows for viewing only a segment of each of the selected one or more physiological signals providing for visualization of a signal property indicated by a parameter measured from each signal of the selected one or more physiological signals within a time window. The presence mode allows for viewing only presence of a feature in each signal of the selected one or more physiological signals within the time window. The presentation control circuit may be configured to present on the display screen a representation of the sensing channels for the selection of the one or more physiological signals and the viewing modes for the selection of the viewing mode, to determine a segment of each signal of the selected one or more physiological signals for presentation according to the selected viewing mode and the time window, and to present the determined segment of the each signal on the display screen.

In Example 2, the subject matter of Example 1 may optionally be configured such that the viewing modes further include a sample mode for viewing a temporal sample of the selected one or more physiological signals sensed within the time window.

In Example 3, the subject matter of any one or any combination of Examples 1 and 2 may optionally be configured such that the viewing modes include the metric mode.

In Example 4, the subject matter of Example 3 may optionally be configured such that the presentation control circuit is configured to receive a selection of the parameter measured from each signal under the metric mode using the user input device.

In Example 5, the subject matter of any one or any combination of Examples 1 to 4 may optionally be configured such that the viewing modes include the presence mode.

In Example 6, the subject matter of Example 5 may optionally be configured such that the presentation control circuit is configured to receive a selection of the feature in the each signal under the presence mode using the user input device.

In Example 7, the subject matter of any one or any combination of Examples 1 to 6 may optionally be configured such that the physiological signals include neural signals each including neural responses evoked by the neurostimulation pulses, and the presentation control circuit is configured to generate the time window with reference to a delivery time for each pulse of the neurostimulation pulses.

In Example 8, the subject matter of Example 7 may optionally be configured such that the neural signals include electrospinogram (ESG) signals, and the neural responses includes electrically evoked compound action potentials (ECAPs).

In Example 9, the subject matter of any one or any combination of Examples 7 and 8 may optionally be configured such that the presentation control circuit is configured to display sensing electrodes on the display screen as the representation of the sensing channels for the selection of the one or more physiological signals and to receive a selection of one or more neural signals by selecting one or more sets of sensing electrodes from the displayed sensing electrodes, the one or more sets of sensing electrodes each used for sensing one signal of the one or more neural signals.

In Example 10, the subject matter of any one or any combination of Examples 7 to 9 may optionally be configured such that the presentation control circuit is configured to display stimulation electrodes in the display screen and to receive a selection of one or more sets of stimulation electrodes from the displayed stimulation electrodes, the one or more sets of stimulation electrodes each used for delivering the neurostimulation pulses.

In Example 11, the subject matter of any one or any combination of Examples 1 to 10 may optionally be configured such that the presentation control circuit is configured to present a time period on the display screen and to receive a setting for the time window being a portion of the presented time period using the user input device.

In Example 12, the subject matter of Example 11 may optionally be configured such that the time period corresponds to an inter-pulse interval between two successive pulses of the neurostimulation pulses.

In Example 13, the subject matter of any one or any combination of Examples 11 and 12 may optionally be configured such that the presentation control circuit is configured to determine a recommendation for the time window based on the timing of the delivery of the neurostimulation pulses and the selected viewing mode and to present the period of time and the recommendation for the time window on the display screen for setting the time window using the user input device.

In Example 14, the subject matter of any one or any combination of Examples 11 to 13 may optionally be configured such that the presentation control circuit is configured to automatically set the time window based on the timing of the delivery of the neurostimulation pulses and the selected viewing mode.

In Example 15, the subject matter of any one or any combination of Examples 1 to 14 may optionally be configured such that the presentation control circuit is configured to determine whether the selected one or more physiological signals are reliable based on stimulation parameters controlling the delivery of the neurostimulation during recording of the selected one or more physiological signals and to present a warning on the display screen in response to a determination that the selected one or more physiological signals are not reliable.

An example (e.g., "Example 16") of a method for delivering neurostimulation pulses and analyzing responses to the delivery is also provided. The method may include storing data representing physiological signals each sensed via a sensing channel of sensing channels, presenting on a display screen of a user interface a representation of the sensing channels for selection of one or more physiological signals from the physiological signals and viewing modes for selection of a viewing mode, receiving the selection of the one or more physiological signals and the selection of the viewing mode using a user input device of the user interface, determining a segment of each signal of the selected one or more physiological signals for presentation according to the selected viewing mode and the time window, and presenting the determined segment of the each signal on the display screen. The viewing modes may include at least one of a metric mode and a presence mode. The metric mode is for viewing only a segment of each of the selected one or more physiological signals providing for visualization of a signal property indicated by a parameter measured from each signal of the selected one or more physiological signals within a time window. The presence mode is for viewing only presence of a feature in each signal of the selected one or more physiological signals within the time window.

In Example 17, the subject matter of the viewing modes as found in Example 16 may optionally include a sample mode for viewing a temporal sample of the selected one or more physiological signals sensed within the time window.

In Example 18, the subject matter of the viewing modes as found in any one or any combination of Examples 16 and 17 may optionally include the metric mode, and the subject matter of any one or any combination of Examples 16 and 17 may optionally further include presenting a plurality of parameters measurable from the each signal on the display screen and receiving a selection of the parameter measured from each signal from the presented plurality of parameters under the metric mode using the user input device.

In Example 19, the subject matter of the viewing modes as found in any one or any combination of Examples 16 to 18 may optionally include the presence mode, and the subject matter of any one or any combination of Examples 16 to 18 may optionally further include presenting a plurality of features of the each signal on the display screen and receiving a selection of the feature in the each signal from the presented plurality of features under the presence mode using the user input device.

In Example 20, the subject matter of the physiological signals as found in any one or any combination of Examples 16 to 19 may optionally include neural signals each including neural responses evoked by the neurostimulation pulses, and the subject matter of any one or any combination of Examples 16 to 19 may optionally further include generating the time window with reference to a delivery time for each pulse of the neurostimulation pulses.

In Example 21, the subject matter of the neural signals as found in Example 20 may optionally include electrospinogram (ESG) signals, and, the subject matter of the neural responses as found in Example 30 may optionally include electrically evoked compound action potentials (ECAPs).

In Example 22, the subject matter of presenting on the display screen the representation of the sensing channels for the selection of the one or more physiological signals as found in any one or any combination of Examples 16 to 21 may optionally include displaying sensing electrodes on the display screen as the representation of the sensing channels for the selection of the one or more physiological signals by selecting one or more sets of sensing electrodes from the displayed sensing electrodes. The one or more sets of sensing electrodes are each used for sensing one signal of one or more neural signals.

In Example 23, the subject matter of any one or any combination of Examples 16 to 22 may optionally further include presenting a time period on the display screen and receiving a setting for the time window being a portion of the presented time period using the user input device.

In Example 24, the subject matter of Example 23 may optionally further include determine a recommendation for the time window based on the timing of the delivery of the neurostimulation pulses and the selected viewing mode and presenting the period of time and the recommendation for the time window on the display screen for setting the time window using the user input device.

An example (e.g., "Example 25") of a non-transitory computer-readable storage medium including instructions, which when executed by a system, cause the system to perform a method for delivering neurostimulation pulses and analyzing responses to the delivery is also provided. The method may include storing data representing physiological signals each sensed via a sensing channel of sensing channels, presenting on a display screen of a user interface a representation of the sensing channels for selection of one or more physiological signals from the physiological signals and viewing modes for selection of a viewing mode, receiving the selection of the one or more physiological signals and the selection of the viewing mode using a user input device of the user interface, determining a segment of each signal of the selected one or more physiological signals for presentation according to the selected viewing mode and the time window, and presenting the determined segment of the each signal on the display screen. The viewing modes may include at least one of a metric mode and a presence mode. The metric mode is for viewing only a segment of each of the selected one or more physiological signals providing for visualization of a signal property indicated by a parameter measured from each signal of the selected one or more physiological signals within a time window. The presence mode is for viewing only presence of a feature in each signal of the selected one or more physiological signals within the time window.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
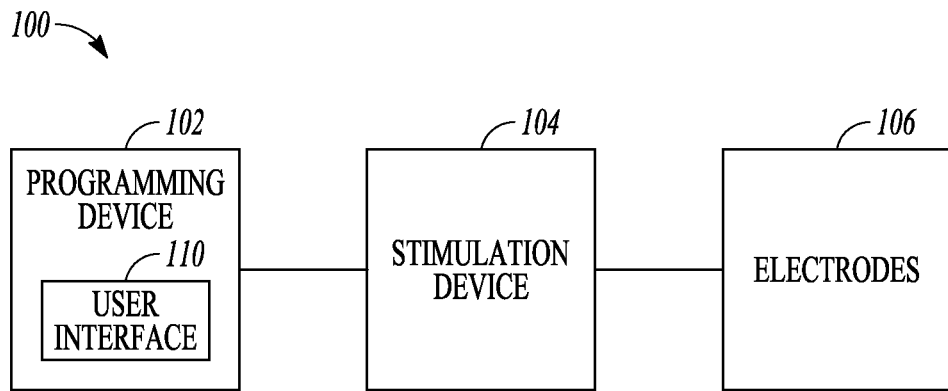
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a user interface for presenting physiological signals and biomarkers for user visualization and assessment. The user interface can be part of a neuromodulation system. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. The user interface according to the present subject matter can be included in such one or more external devices. While the application in the neuromodulation system is discussed as an example, the present subject matter can used in any application in which physiological signals and biomarkers are analyzed.

Physiological signals and biomarkers, such as stimulus artifact, evoked neural response, and spontaneous neural responses, can contain important predictive information on therapy efficacy, but can also be complex and difficult to interpret by a user or a machine in their raw forms. While such physiological signals and biomarkers are used in some instances to control delivery of neurostimulation in a closed-loop system, there is still a need for presenting them in manners facilitating their analysis, such as by providing for visualization that allows for efficient classification of neural responses.

The present subject matter provides for a method and user interface for presenting salient characteristics of a biomarker signal to a user to enable the user to perform various tasks such as:

identifying a time interval over which a specified parameter can be visualized and measured from a sensed physiological signal;

identifying in space a collection of electrodes over which a specified parameter can be visualized and measured from a sensed physiological signal;

classifying (e.g., using predetermined templates) a biomarker based on an absolute or relative measure (e.g., an artifact, a propagating signal, a spontaneous activity, etc.) over time or over space; and grading the biomarker for signal fidelity and/or correlation to a therapy (e.g., in conjunction with patient ratings, an electronic record, etc.).

In this document, unless noted otherwise, a "patient" includes a person receiving treatment delivered from, and/or monitored using, a neurostimulation system according to the present subject matter, and a "user" includes a physician or other caregiver who examines and/or treats the patient using the neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for SCS applications. While an SCS system is illustrated and discussed as an example, the present subject matter applies to any neurostimulation system with electrodes placed in locations suitable for sensing one or more neural signals from which indications of degenerative and/or other nerve diseases can be detected and monitored.

Figure 2:
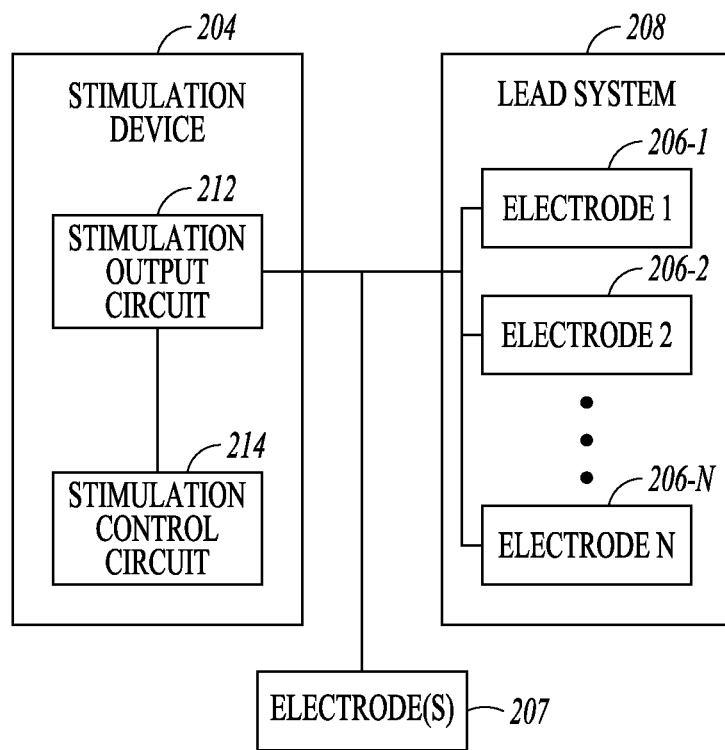
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and optionally electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Lead and electrode configurations are illustrated in this document as examples and not limitations. For example, various embodiments can use paddle electrodes, cuff electrodes, and other electrodes suitable for delivering neurostimulation.

Figure 3:
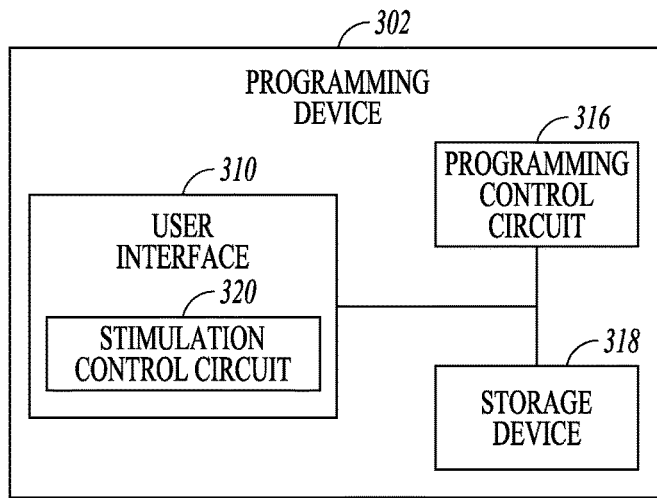
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit can include, but is not limited to, a microprocessor or a portion thereof, a microcontroller or portions thereof, and/or a programmable logic circuit or a portion thereof.

Figure 4:
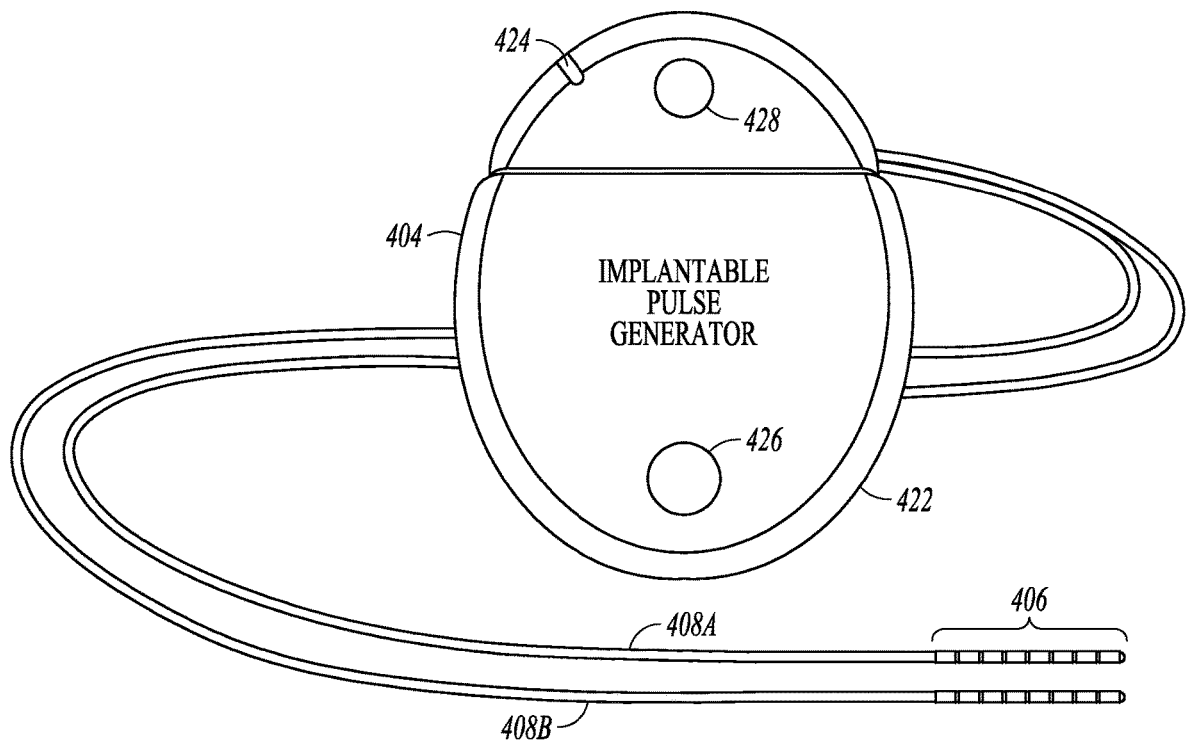
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to target nerve cells in the subject's spinal cord.

Figure 5:
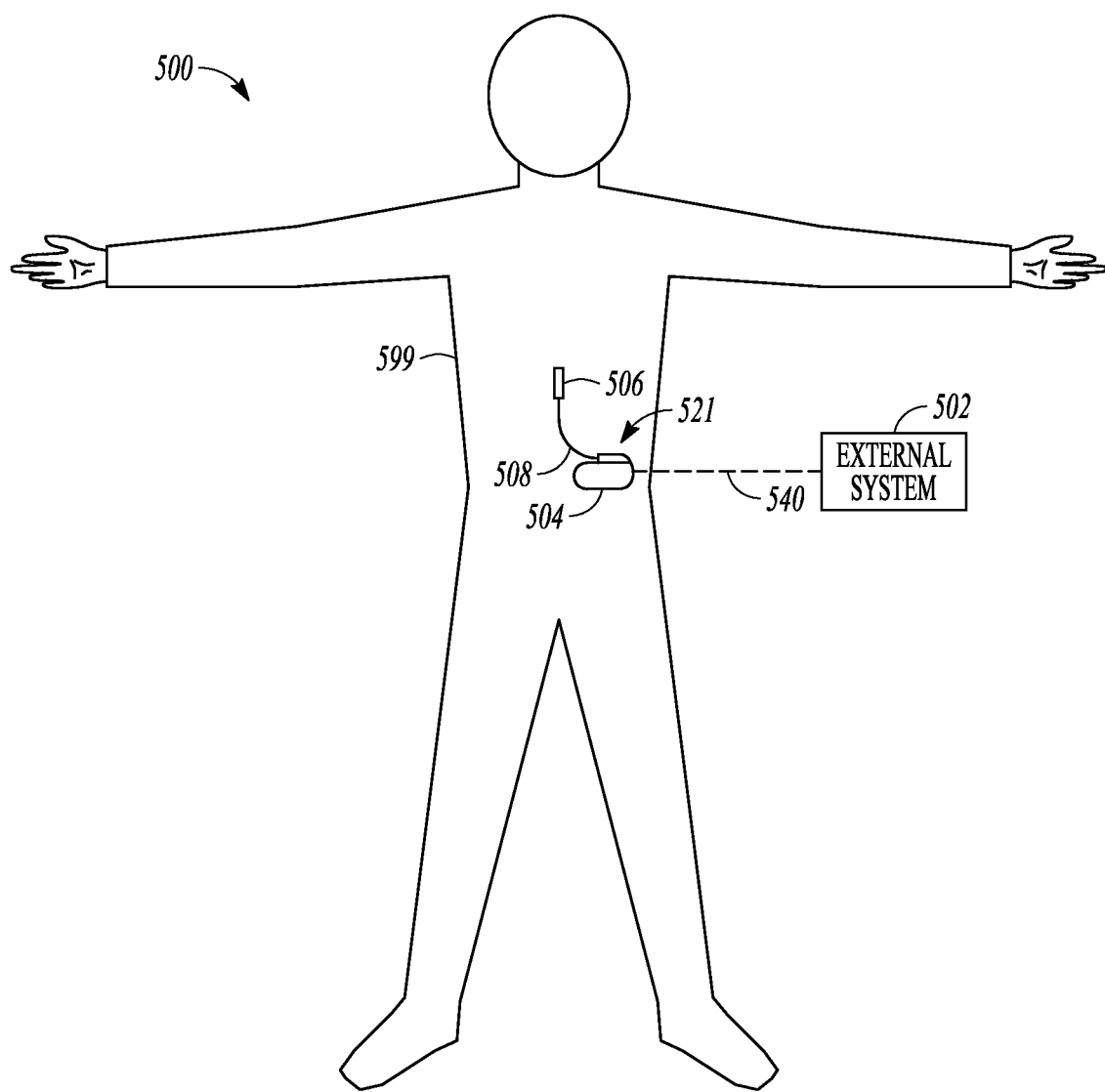
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external system 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode.

Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
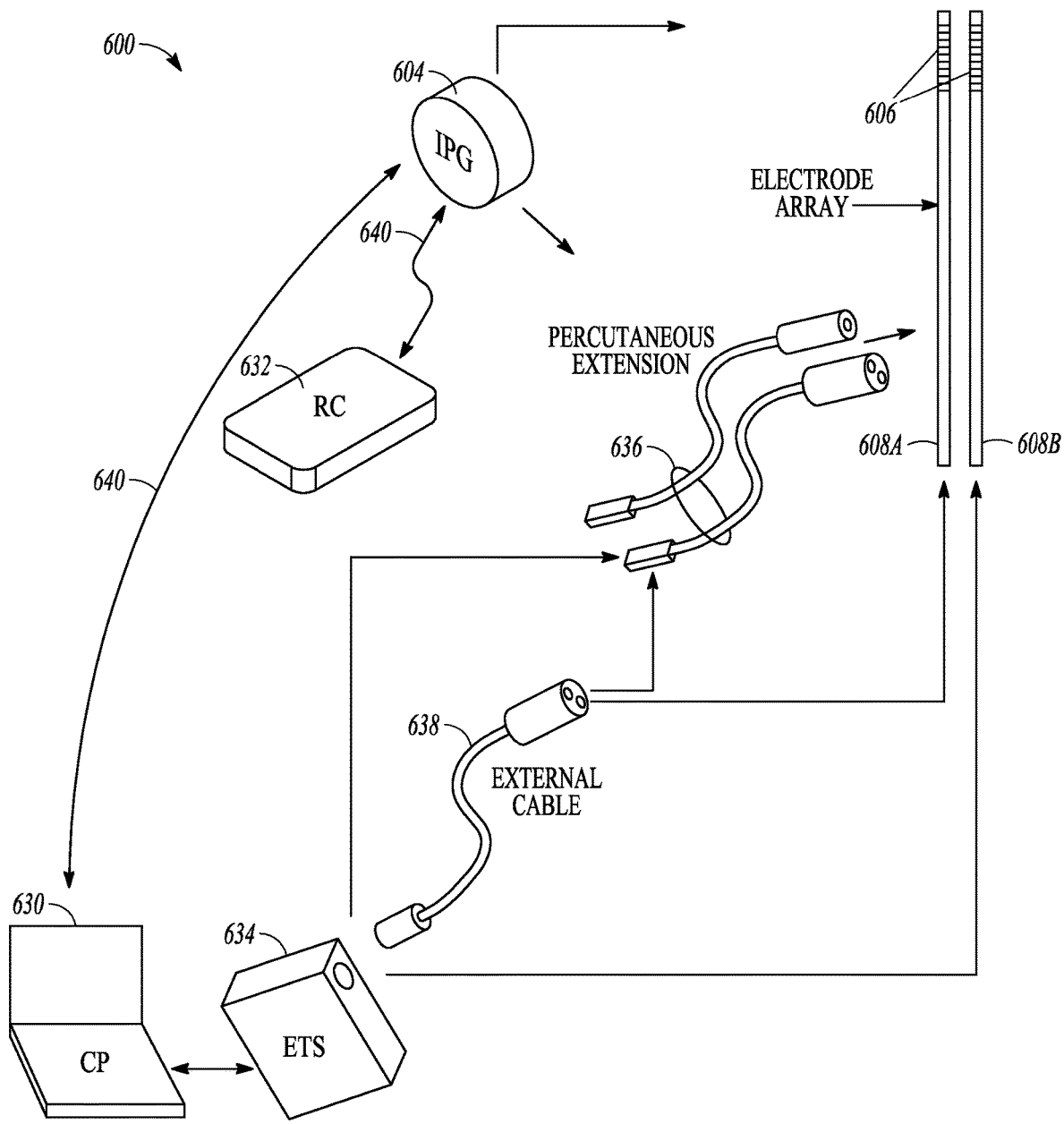
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device configured for ambulatory use and may be used as a preliminary stimulator after leads 408A and 4083 have been implanted and used prior to stimulation with IPG 604 to test the patient's responsiveness to the stimulation that is to be provided by IPG 604. ETS 634 may include cable connectors allowing it to readily interface the proximal end of external leads that are chronic use, and may include replaceable batteries.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$, is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
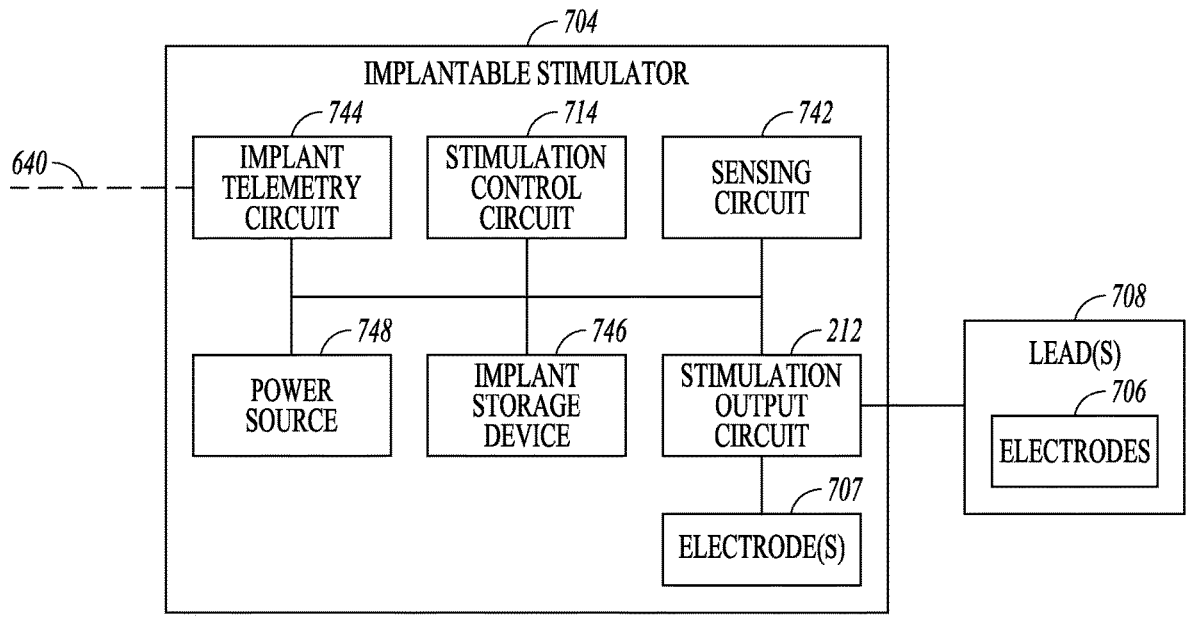
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742 senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. In various embodiments, sensing circuit 742 senses one or more neural signals and detects one or more indications of a neurodegenerative disease, as further discussed with reference to FIGS. 9-16. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
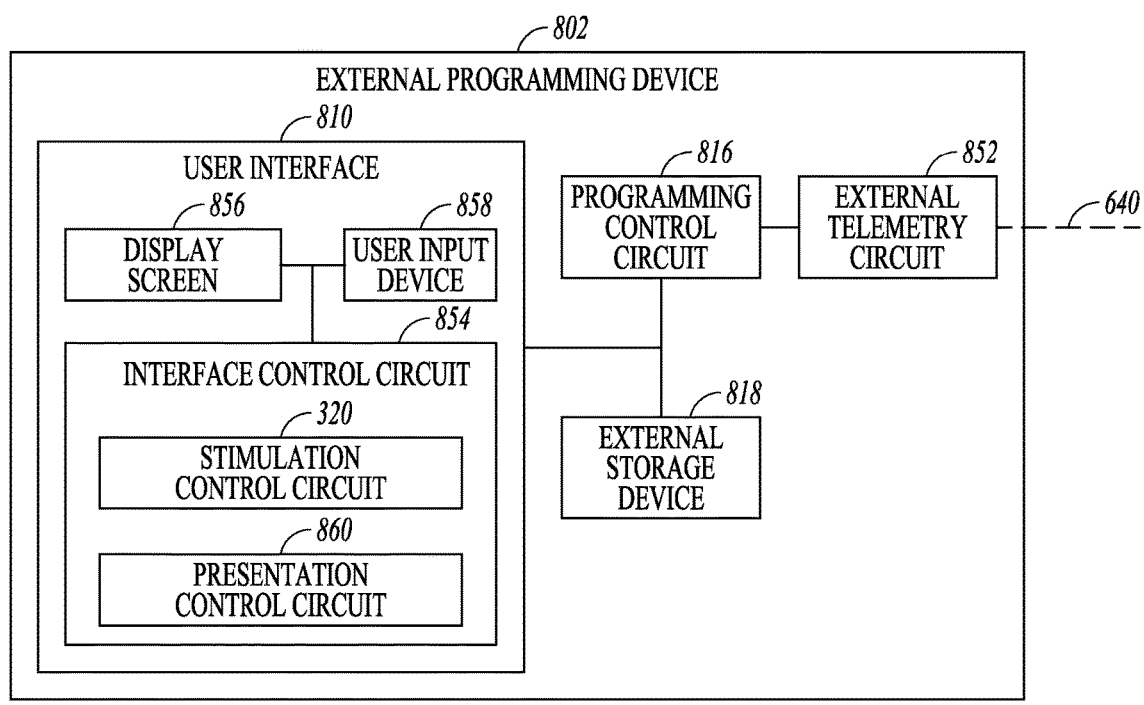
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 can include stimulation control circuit 320 and a presentation control circuit 860. Presentation control circuit 860 can, for example, control presentation of the one or more physiological signals sensed using sensing circuit 742 on display screen 856 based on settings including user selections entered using user input device 858, as further discussed below with reference to FIGS. 9-14. In various embodiments, depending on various diagnostic and/or therapeutic needs, interface control circuit 854 can include either one of both of stimulation control circuit 320 and presentation control circuit 860.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
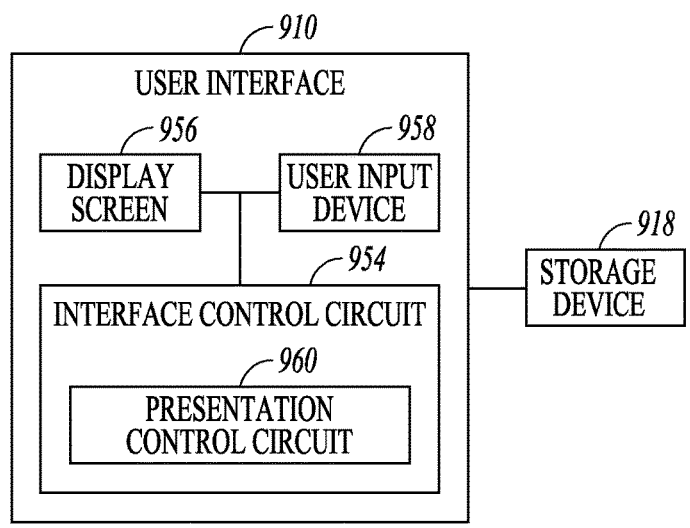
FIG. 9 illustrates an embodiment of a user interface for analyzing one or more physiological signals, such as a user interface of the implantable neurostimulation system of FIG. 6.

FIG. 9 illustrates an embodiment of a user interface 910 for analyzing one or more physiological signals. User interface 910 can be a user interface of a neurostimulation system such as system 600, and can be implemented in a programming device such as external programming device 802. The one or more physiological signals can be selected from physiological signals stored in a storage device 918. Storage device 918 can be a storage device of the neurostimulation system such as system 600, and can be implemented in a storage device such as external storage device 818. However, a system for analyzing physiological signals that includes user interface 910 and storage device 918 can be implemented in any dedicated or generic computing device that includes a user interface and a storage device.

Storage device 918 can store data representing physiological signals each sensed via a sensing channel of sensing channels. A sensing channel can be configured for sensing a physiological signal, such as a biopotential signal, using a set of electrodes. In various embodiments, the set of electrodes can be defined by stimulation parameters programmable by the user.

User interface 910 includes a user input 958, a display screen 956, and an interface control circuit 954. User input device 958 can represent an example of user input device 858 and can be of a type discussed for user input device 858 above. Display screen 856 can represent an example of display screen 856 and can be of a type discussed for display screen 856 above. Interface control circuit 954 can represent an example of interface control circuit 954 and includes a presentation control circuit 960, which can represent an example of presentation control circuit 860. In various embodiments, interface control circuit 954 can optionally include stimulation control circuit 320.

User input device 958 can receive a selection of one or more physiological signals from the physiological signals stored in storage device 918 and a selection of viewing mode from viewing modes including at least one of a metric mode and a presence mode. The metric mode is for viewing only a segment of each of the selected one or more physiological signals and provides for visualization of a signal property indicated by a parameter measured from each signal of the selected one or more physiological signals within a time window. The presence mode is for viewing only presence of a feature in each signal of the selected one or more physiological signals within the time window. Presentation control circuit 960 can present on the display screen a representation of the sensing channels for the selection of the one or more physiological signals and the viewing modes for the selection of the viewing mode, can determine a segment of each signal of the selected one or more physiological signals for presentation according to the selected viewing mode and the time window, and can present the determined segment of the each signal on the display screen.

The viewing modes can also include a sample mode for viewing a temporal sample of the selected one or more physiological signals sensed within the time window. In various embodiments, the viewing modes available for selection by the user can include (i) the sample mode, (ii) the metric mode, (iii) the presence mode; (iv) the sample and metric modes, (v) the sample and presence modes, (vi) the metric and presence modes, (vii) the sample, metric, and presence modes.

User interface 910 can present one or more biomarker signals as the one or more physiological signals in manners selected by the user to allow for visualization of various salient characteristics of the biomarker signal. In various embodiments, the physiological signals stored in storage device 918 can include neural signals each include neural responses evoked by neurostimulation pulses. Presentation control circuit 960 can generate the time window with reference to a delivery time for each pulse of the neurostimulation pulses. An example of the neural signals includes electrospinogram (ESG) signals, and a corresponding example of the neural responses includes electrically evoked compound action potentials (ECAPs). The ECAPs can be biomarkers for neural responses to neurostimulation such as SCS. ESG signal with ECAP is discussed as an example, but not as a limitation, in this document for illustrative purposes. In various embodiments, the present subject matter can be applied in presentation and analysis of various physiological signals, as those skilled in the art will understand upon reading this document.

ESG is a recording of electrical activity from the spinal cord. Many nerve cells produce low-level electrical signals, called action potentials, that form electrical activity patterns and in many instances can have an additive effect producing a magnified neural response. An example is the ECAP, which is evoked by a stimulation such as a neurostimulation pulse and results from many neural cells firing simultaneously or close in time. An ESG signal also include neural components having a random appearance and representing activities of many different types of cells of the patient's nervous system that spontaneously fire over the time. The ESG signal further includes non-neural components representing various physical movements of the patient, such as movements associated with cardiac activities, respiratory activities, and skeletomuscular activities.

An ESG signal can be sensed non-invasively using surface electrodes attached to the patient's skin. This surface sensing usually requires an amplifier with high gain and high signal-to-noise ratio (SNR). An ESG signal can also be sensed invasively using electrodes incorporated onto one or more percutaneous or implantable leads. In one example, the ESG signal is sensed epidurally using epidural electrodes placed adjacent or over the dura, which is a membrane structure surrounding the spinal cord and the cerebral cortex of the patient. In another example, the ESG signal is sensed intradurally using a lead that penetrates the dura such that the electrodes can be placed subdurally within the spinal cord.

Findings from recent clinical studies suggest fast acting pain relief can be achieved by using SCS with active recharge waveforms with intensity just below the threshold for paresthesia resulting from dorsal column activation. ESG signals can be sensed from the patient to obtain characteristics (e.g., amplitude and shape) of the patient's dorsal column response to the stimulation, and therefore can be used for evaluation of stimulation parameters (e.g., waveforms and tissue sites of stimulation) to select a suitable pattern of stimulation. It has been observed that the neural responses evoked by SCS with active recharge waveforms exhibit an increasing magnitude and a changing shape as the stimulation increases and changes, respectively, with stimulation amplitude, stimulation pulse width, and/or closeness of stimulation site to the spinal cord. Dorsal column fibers of different diameters are known to produce a neural response after different delays, with fibers of smaller diameters associated with greater delays. The ECAP detectable from the ESG is a result of additive effect of the multiple action potentials produced by different axons of different diameters firing with different delays. The present subject matter can assist, for example, in analysis of ECAPs as presented in ESG for effectiveness of neurostimulation and selection of a suitable set of stimulation parameters controlling the neurostimulation for a patient.

Figure 10:
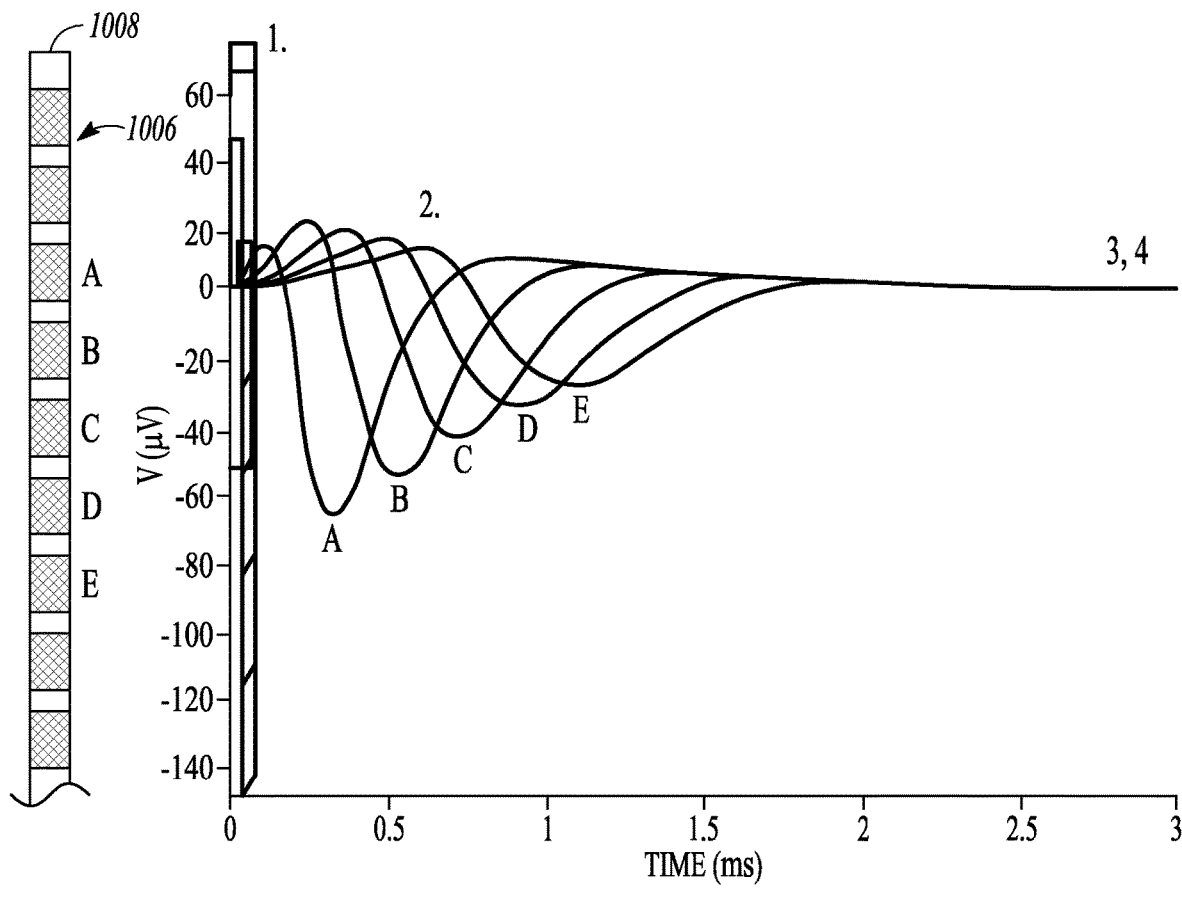
FIG. 10 illustrates an example of neural signals sensed using different electrodes on a lead and including neural response to a neurostimulation pulse.

FIG. 10 illustrates an example of neural signals sensed using different electrodes 1006 on a lead 1008. The neural signals include neural responses to a neurostimulation pulse. Lead 1008 can represent a lead in lead system 208 including its various embodiments as discussed in this document. Electrodes 1006 can represent an example of electrodes 206 including their various embodiments as discussed in this document. Shown in FIG. 10 is an example of ESG sensed using each of electrodes A-E of electrodes 1006 in lead 1008 for delivering SCS and sensing neural responses to SCS. ECAPs in response to a neurostimulation pulse as sensed by each of electrodes A-E are shown as labeled with "A"-"E", respectively. As distinct types of stimulation-related signals or signal components manifest differently in space over time, visualization of each distinct type can be made possible by controlling presentation of the signals. As illustrated in FIG. 10, examples of such distinct types of stimulation-related signals or signal components include (with the following item numbers marked):

1. Stimulus artifact (a stimulus such as a pulse as recorded in the sensed ESG signal). An artifact is quasi-static (fixed time points), has a fixed duration based on the stimulus, decays in space, is centered on stimulation electrode(s), and has the largest amplitude among the signals.
2. Evoked signal (neural response evoked by the stimulus). An evoked signal propagates in predictable time window from the stimulation electrode(s). Its width may increase, while its amplitude and power may decrease over propagation (dispersion).
3. Spontaneous signal (above noise). A spontaneous signal likely manifests as increased overall power. Power of the spontaneous signal on leads may noticeably change above background noise. The spontaneous signal has distinct spectral properties, and the effects are not necessarily monotonic.
4. Background noise. After averaging the sensed ESG, effects elicited by postural changes or spinal cord movement in the spinal canal can be demonstrated. Power of the background noise on all leads may have a subtle change.

Different spatial and temporal characteristics of these distinct types of stimulation-related signals or signal components allow them to be classified, visualized, and analyzed. User interface 910 can provide the user with an intuitive approach to configuring space and time windows as thresholding settings for presenting signal segments of interest.

A "signal metric" according to the present subject matter can refer to and include any one or more of the following parameters measured from the ECAP portion of ESG:
  peak amplitude (amplitude of a negative or positive peak of an evoked response);
  area under curve (the area between the ESG signal and a baseline for an evoked response or another specified period, also referred to curve area in this document), which can be determined using:

$$A = \sum_{n=1}^{N} |y(n)|,$$

where A is the area under the curve, is the time index, $\gamma$ is the data time series, and N is the index of the last data sample in the time series;
  Parseval's or Fourier and spectral power;
  N1-P2 amplitude (the difference between amplitudes of N1 and P2, where N1 is the first negative peak in an evoked response that is correlated to the response of faster fibers such as Aβ fibers and myelinated fibers, and P2 is the second positive peak in the evoked response that is correlated with response of slower fibers) (or $N_{peak}$-$P_{peak}$, where "peak" is arbitrary);

curve length (duration of an evoked response measured from the ESG signal), which can be determined using:

$$CL = \sum_{n=2}^{N-1} |y(n) - y(n-1)|,$$

where CL is the curve length;

higher order clustering metric (e.g., .PCA value, cluster metric), and/or any of the features above over a pre-specified time interval (which can include the stimulus artifact, a spontaneous or evoked neural response, and/or the background). Using a time interval there is no need to pay attention to whether the ESG contains artifact, or evoked response, or spontaneous response, or noise.

The signal metric can further include reliability parameters calculated from any one or more parameters listed above for indicating differences and/or errors, such as one or more of the following:

difference;

mean squared error;

standard deviation from mean or median over samples;

correlation of functions;

R squared from regression to function type;

a clustering reliability metric (e.g., gap index or silhouette index) for signal classification;

minimum-to maximum range of the ESG signal over a predefined time window (e.g., this can include the N1-P2 amplitude);

delay of the ECAP relative to the stimulation pulse (i.e., a significantly variable delay indicates unreliable signal); and/or other characteristics of the ESG signal as compared to a pre-loaded references taken from literature.

Figure 11:
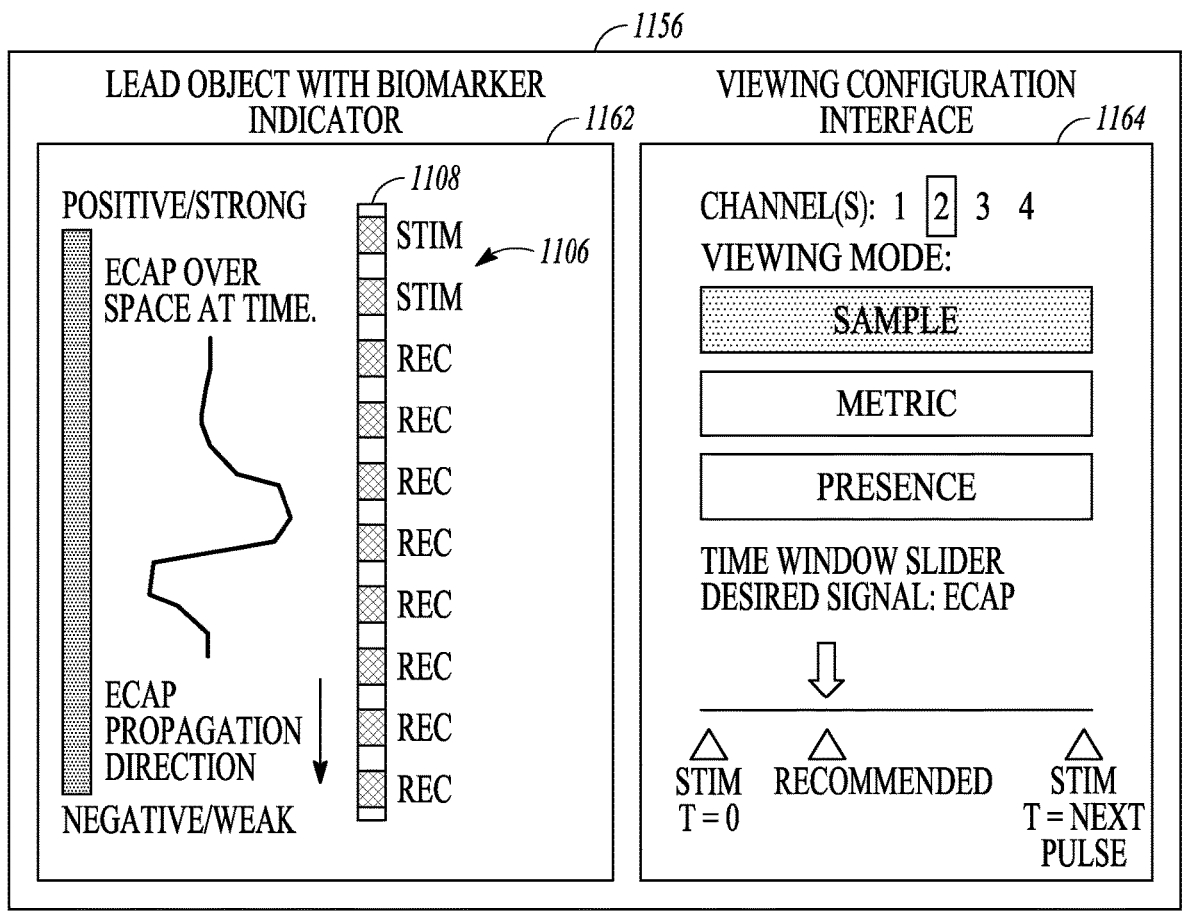
FIG. 11 illustrates an embodiment of portions of a display screen of a user interface, such as the user interface of FIG. 9, under a viewing mode.
Figure 12:
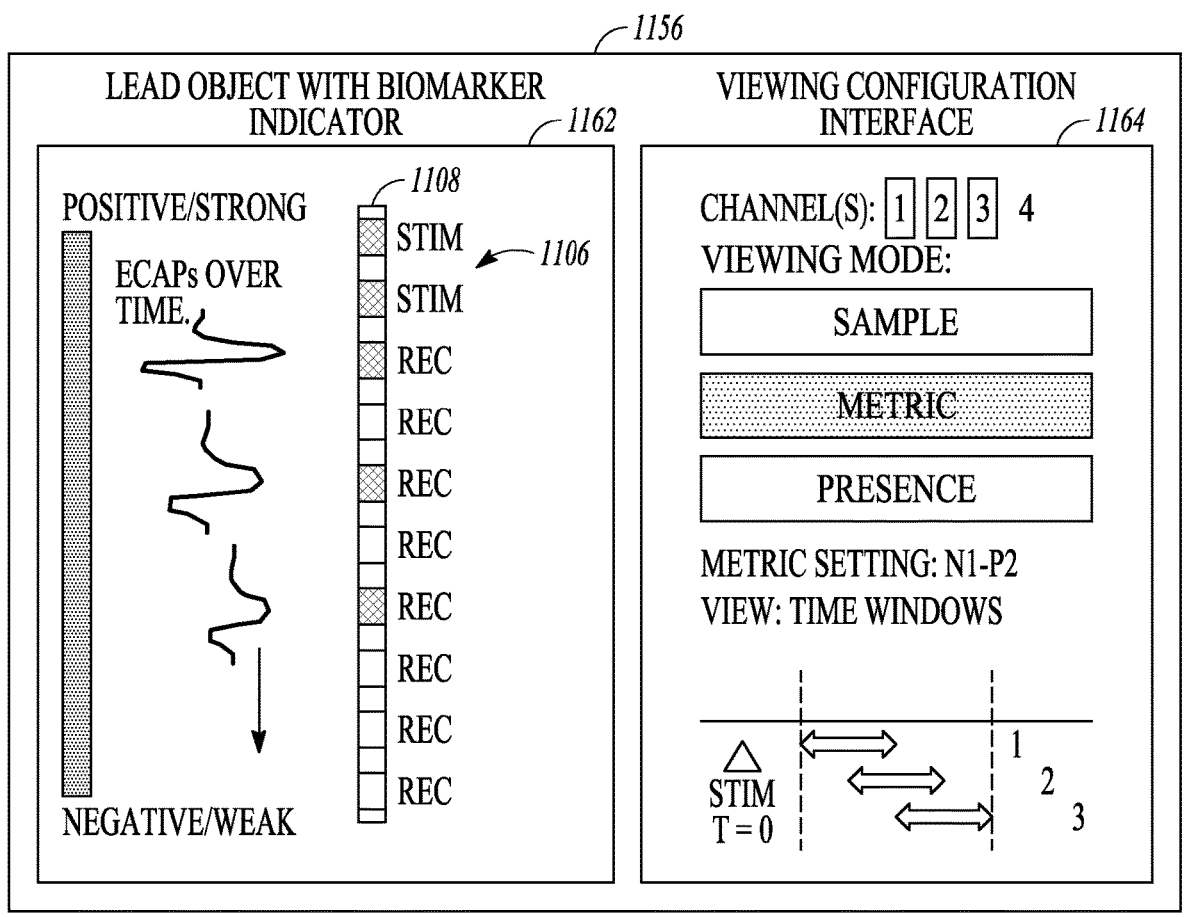
FIG. 12 illustrates an embodiment of the portions of the display screen of FIG. 11 under another viewing mode.
Figure 13:
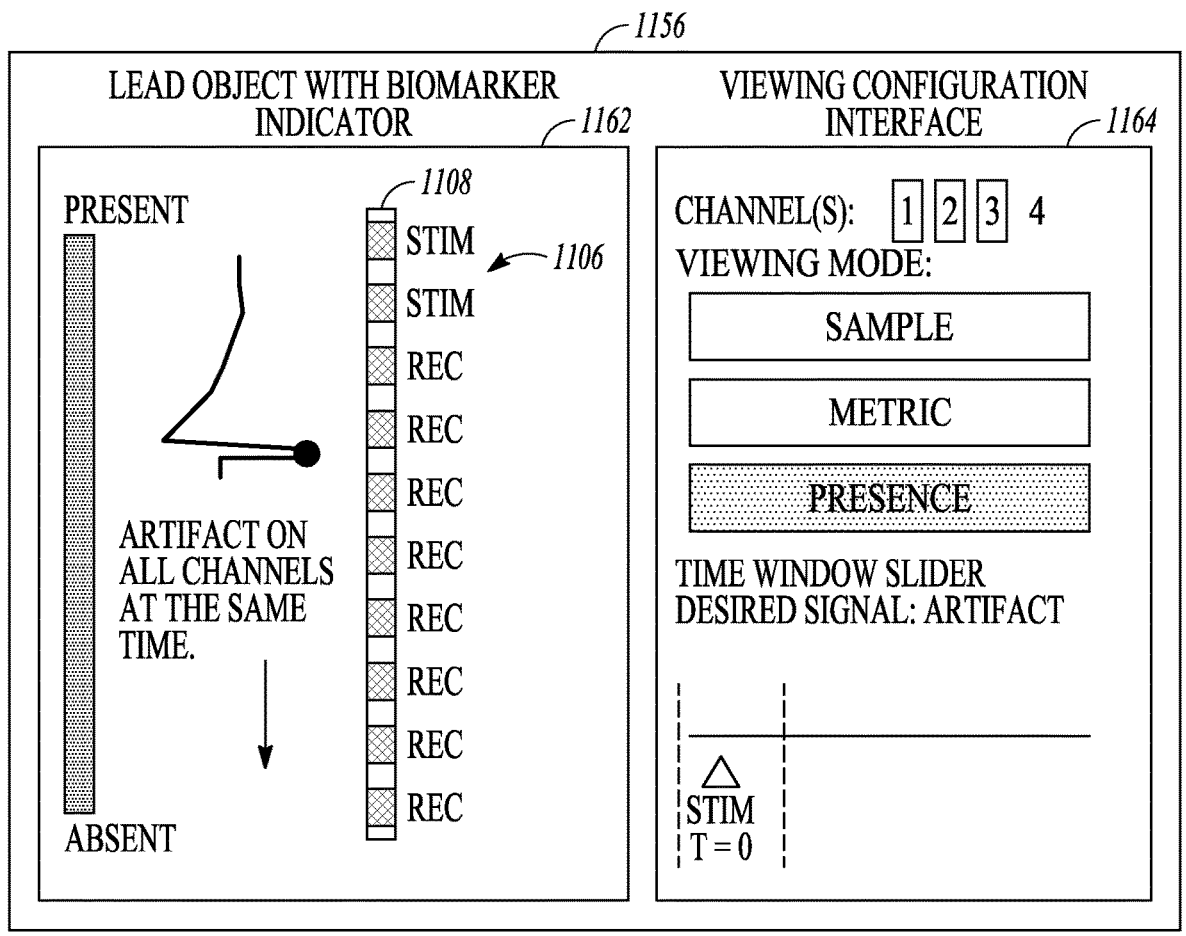
FIG. 13 illustrates an embodiment of the portions of the display screen of FIG. 11 under yet another viewing mode.

FIGS. 11-13 each illustrate an embodiment of portions of a display screen 1156 of a user interface, such as user interface 910, with one of several viewing modes being selected. Display screen 1156 can represent an example of display screen 956. In the illustrated embodiments, a "lead object with biomarker indicator" area 1162 and a "viewing configuration interface" area 1164 are presented on display screen 1156. Area 1164 presents (1) sensing channel numbers (1-4 shown for example) for the user to select for displaying the segment of each of the one or more physiological signals, (2) viewing modes ("sample", "metric", and "presence" shown for example) for the user to select a viewing mode, and (3) a time period for the user to specify the time window and a "desired signal" field for the user to enter the signal or signal component of interest. Each channel number is associated with a set of sensing electrodes selected from electrodes 1106 of lead 1108 displayed in area 1162. In some embodiments, the user can select the channel by selecting the set of the sensing electrodes. The list of viewing modes available to be selected from can include any one or more of the sample, metric, and presence viewing modes as well as other viewing modes as desired and implemented by those skilled in the art. In the illustrated embodiment, the user can specify the time window using the displayed time window slider, and a recommendation for the time window determined automatically based on the viewing mode and the desired signal is also displayed. Area 1162 presents representation of lead 1108 including electrodes 1106. In the illustrated embodiment, lead 1108 represents a single percutaneous or implantable lead for delivering SCS and sensing ESG. Each electrode of electrodes 1106 is labeled as a stimulation electrode (STIM) or sensing (recording) electrode (REC). In various embodiments, each electrode of electrodes 1106 can be designated as a stimulation electrode and/or a sensing electrode (e.g., an electrode can be used for stimulation and sensing at different times). Area 1162 also represents segment(s) of one or more ESG signals as determined based on the selected viewing mode and the specified time window.

FIG. 11 illustrates the portions of display screen 1156 when the sample mode is selected. The sample mode (also referred to as the "snapshot-in-time" mode) provides for viewing of a temporal sample ("snapshot in time") of the selected ESG signal(s) sensed within the specified time window and including the specified desired signal. In the illustrated example, area 1164 shows that sensing channel 2 is selected, ECAP is selected as the desired signal, and the time window starts at the delivery time of the neurostimulation pulses. A recommended end of the time window is determined based on the desired signal and displayed to the user, who can specify the time window by moving the time winder slider. Area 1162 shows a time sample ("snapshot") of the ESG signal sensed through sensing channel 2 and including an ECAP (the desired signal).

FIG. 12 illustrates the portions of display screen 1156 when the metric mode is selected. The metric mode (also referred to as the "metric only" mode) provides for viewing only a segment of each of the selected ESG signal(s) providing for visualization of a signal property indicated by a parameter measured from each of the selected ESG signal (s) within the time window. In the illustrated example, area 1164 shows that sensing channels 1, 2, and 3 are selected, the N1-P2 amplitude is selected as the parameter (metric setting), and the time window starts at the delivery time of the neurostimulation pulses. A recommended end of the time window is determined based on the selected parameter and displayed to the user, who can specify the time window by moving the time winder slider for each of the selected sensing channels 1, 2, and 3. Area 1162 shows a segment of each of the ESG signals sensed through the selected sensing channels 1, 2, and 3. The three displayed segments provide for visualization of the signal property indicated by the N1-P2 amplitude measured from each of the ESG signals sensed through the selected sensing channels 1, 2, and 3 within the specified time window (showing only a segment of each ESG signal to focus the visualization on the signal property). In various embodiments, the parameter (metric setting) can be chosen from a list of parameters included in the signal metric for ECAP in ESG as discussed above.

FIG. 13 illustrates the portions of display screen 1156 when the presence mode is selected. The presence mode (also referred to as the "presence only" mode) allows for viewing only presence of a selected feature in each of the selected ESG signal(s) within the time window. In the illustrated example, area 1164 shows that sensing channels 1, 2, and 3 are selected, stimulus artifact (artifact) is selected as the desired signal (i.e., the feature), and the time window starts at the delivery time of the neurostimulation pulses. Area 1162 shows the stimulus artifact that is sensed through all the selected sensing channels 1, 2, and 3 at the same time, thereby indicating the presence of the stimulus artifact. In various embodiment, the desired signal (i.e., the feature) can be selected from a list of features. Examples for such features include the stimulus artifact, ECAP, time intervals, and user-specified time intervals. In some embodiments, one or more thresholds for detecting the selected feature can be specified by the user.

Referring back to FIG. 9, user interface 910 can be configured to support the presentation features illustrated in FIGS. 11-13 by way of example, but not by way of restriction. User input device 958 can receive the various user inputs discussed with reference to FIGS. 11-13. Display screen 965 can accommodate needs for presenting areas 1162 and 1164 as illustrated in FIGS. 11-13. Presentation control circuit 960 can be configured to present the contents of areas 1162 and 1164 in response to the user inputs.

In various embodiments, user input device 958 can receive a selection of one or more physiological signals from the physiological signals stored in storage device 918. This selection can be made by selecting one or more sensing channels. The one or more physiological signals can be one or more neural signals each including neural responses evoked by neurostimulation pulses delivered to the patient. Examples of the one or more neural signals include one or more ESG signals each including ECAPs. In some embodiments, user input device 958 can also receive the selection of one or more neural signals by selecting one or more sets of sensing electrodes from electrodes available for sensing. The one or more sets of sensing electrodes are each used for sensing one of the one or more neural signals and are each corresponding to a sensing channel. In some further embodiments, user input device 958 can also receive a selection of one or more sets of stimulation electrodes from electrodes available for stimulation. The one or more sets of stimulation electrodes are each used for delivering the neurostimulation pulses and are each corresponding to a stimulation channel. Thus, the one or more neural signals can each be associated with a user-selectable sensing channel (or set of sensing electrodes) and/or a user-selectable stimulation channel (or set of stimulation electrodes). The electrodes available for sensing and the electrode available for stimulation can include the same electrodes, such as the electrodes on a percutaneous or implantable lead for SCS. User input device 958 can also receive a selection of a viewing mode from available viewing modes. The available viewing modes can include any one or any combination of the sample mode, the metric mode, the presence mode, and one or more other viewing modes supported by user interface 910. User input device 958 can also receive a setting for the time window when the time window is not set automatically by presentation control circuit 960.

In various embodiments, presentation control circuit 960 can present on display screen 956 the sensing channels (e.g., each represented by a channel number) for the selection of the one or more physiological signals and the viewing modes for the selection of the viewing mode. Presentation control circuit 960 can determine a segment of each signal of the selected one or more physiological signals for presentation according to the selected viewing mode and the time window and can present the determined segment of the each signal on display screen 956. Under the metric mode, presentation control circuit 960 can present available parameters on display screen 956 for the selection of the parameter (e.g., metric setting in FIG. 12) and, after receiving the selection, determine the segment to allow for focused visualization of features of each signal from which the selected parameter is measured. Under the presence mode, presentation control circuit 960 can present available parameters on display screen 956 for the selection of the feature (e.g., desired signal in FIG. 13) and, after receiving the selection, determine the segment to allow for focused visualization of presence of the selected feature in each signal. In some embodiments, presentation control circuit 960 can detect the selected feature using one or more thresholds that can be, for example, set and/or adjusted automatically or by the user using user input device 958. In one embodiment, presentation control circuit 960 determines a recommendation or default for the one or more thresholds and presents the recommendation on display screen 956 for the user to determine the one or more thresholds using user input device 958.

In various embodiments, presentation control circuit 960 can generate the time window. Presentation control circuit 960 can present a period of time on display screen 956 for the user to set the time window using user input device 958. When the selected one or more physiological signals include one or more neural signals, the presented period of time can, for example, correspond to an inter-pulse interval between two successive pulses of the neurostimulation pulses, and presentation control circuit 960 can determine a recommendation for the time window based on the timing of the delivery of the neurostimulation pulses and the selected viewing mode. Presentation control circuit 960 can determine the recommendation, for example, based on a timing of the specified desired signal relative to timing of delivering the neurostimulation pulses under the sample mode, based on timing of the selected parameter under the metric mode, and based on timing of the selected feature under the presence mode. After the recommendation is determined, presentation control circuit 960 can present the period of time and the recommendation for the time window on display screen 956 for setting the time window, and user input device 958 can receive the setting of the time window from the user. In one embodiment, presentation control circuit 960 can automatically set the time window. For example, after the recommendation is determined, presentation control circuit 960 can generate the time window according to the recommendation without receiving the setting from the user.

In various embodiments, presentation control circuit 960 can determine whether selections and/or settings received by user input device 958 are inadequate or unavailable. Presentation control circuit 960 can present a warning message 956 on display screen 956 to allow corrections by the user using user input device 958. When the selections and/or settings received from the user cannot be accommodated, presentation control circuit 960 can revert to operation according to a previous (e.g., the last) setting or to signal sensing without presentation under any of the viewing modes.

In various embodiments, presentation control circuit 960 can determine whether the selected one or more neural signals are reliable based on stimulation parameters controlling the delivery of the neurostimulation during sensing of the selected one or more neural signals. When the signal reliability is in questionable, presentation control circuit 960 can present a warning on display screen 956 for the user to make adjustments. In various embodiments, a signal and metric can be considered to be "unreliable" when, for example, one or more of their characteristics are above or below pre-determined threshold(s), a feature occurs earlier or later than expected, and/or they exhibit excessive variability. For example, an "unreliable" ECAP may exhibit an unusually low amplitude (e.g., less than 5 microvolts peak-to-peak), amplitudes that fluctuate by more than 100% over a small number (e.g., 10) of acquisitions along with an unusually short (less than 5 samples) width and wildly fluctuating delays relative to the stimulation regardless of the distance between the stimulation and sensing channels (e.g., 0.5 to 2 ms). In contrast, a more reliable ECAP may be larger (e.g., at least 40 microvolts peak-to-peak), only exhibit an amplitude fluctuation of less than 50% over those 10 samples, exhibit a consistent moderate width (e.g., 25 samples), and exhibit a consistent delay that corresponds to the electrode from which the signal is sensed. (e.g. based on expected conduction velocity).

Figure 14:
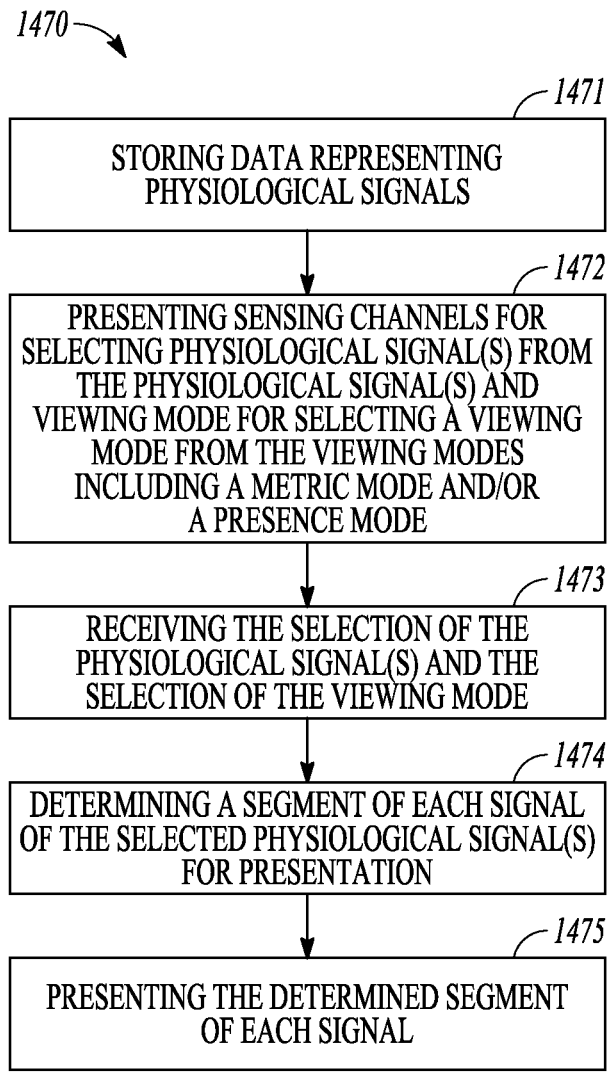
FIG. 14 illustrates an embodiment of a method for analyzing one or more physiological signals.

FIG. 14 illustrates an embodiment of a method 1470 for analyzing one or more physiological signals. Method 1470 can be performed using a user interface and a storage device, such as user interface 910 and storage device 918. In one embodiment, storage device 918 can include a non-transitory computer-readable storage medium including instructions, which when executed by a processor of interface control circuit 954, cause the processor (or portion thereof, including presentation control circuit 960) to perform method 1470. In various embodiments, method 1470 is performed for purposes of determining whether or how to deliver a neurostimulation therapy to a patient.

At 1471, data representing physiological signals each sensed from the patient via a sensing channel of sensing channels are stored. Examples of the physiological signals include neural signals each including neural responses evoked by neurostimulation pulses delivered to the patient. An examples of the neural signals includes ESG signal with the neural responses including ECAPs, such that when the patient receives SCS.

At 1472, a representation of the sensing channels (e.g., channel numbers and/or sensing electrodes) are presented on a display screen of the user interface for selection of one or more physiological signals from the stored physiological signals. Viewing modes are also presented on the display screen for selection of a viewing mode. The viewing modes includes at least one of a metric mode or a presence mode. The metric mode provides for viewing only a segment of each of the selected one or more physiological signals providing for visualization of a signal property indicated by a parameter measured from each signal of the selected one or more physiological signals within a time window. The presence mode provides for viewing only presence of a feature in each signal of the selected one or more physiological signals within the time window. The viewing modes can optionally further include a sample mode. The sample mode provides for viewing a temporal sample of the selected one or more physiological signals sensed within the time window. Under the metric mode, a plurality of parameters measurable from each selected signal is presented on the display screen, and a selection of the parameter measured from the presented plurality of parameters is received using the user input device. Under the presence mode, a plurality of features of each signal is presented on the display screen, and a selection of the feature from the presented plurality of features is received using the user input device.

At 1473, the selection of the one or more physiological signals and the selection of the viewing mode are received using a user input device of the user interface. When the selected one or more physiological signals include one or more neural signals selected from the neural signals each including the neural responses, the time window can be generated with reference to a delivery time for each pulse of the neurostimulation pulses. For example, a time period can be presented on the display screen, and a setting for the time window being a portion of the presented time period can be received from the user using the user input device. A recommendation for the time window can be determined automatically based on the timing of the delivery of the neurostimulation pulses and the selected viewing mode. Then the period of time and the recommendation for the time window are both displayed on the display screen for setting the time window by the user using the user input device. The time window can also be set automatically according to the recommendation.

At 1474, a segment of each signal of the selected one or more physiological signals is determined for presentation according to the selected viewing mode and the time window. At 1475, the determined segment of the each signal is presented on the display screen. Examples of the presentation include those illustrated in FIGS. 11-13.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neurostimulation pulses and analyzing responses to the delivery, the method comprising:
   receiving data representing an electrospinogram (ESG) signal including electrically evoked compound action potentials (ECAPs) evoked by the neurostimulation pulses;
   presenting on a display screen viewing modes including:
      a metric mode for viewing the ESG signal providing for visualization of a signal property indicated by an ECAP parameter determined using an ECAP portion of the ESG signal within a time window for the metric mode, the ECAP portion of the ESG signal including an ECAP of the ECAPs; and
      a presence mode for viewing the ESG signal providing for visualization of presence of a feature in the ESG signal within a time window for the presence mode;
   receiving a selection of a viewing mode from the presented viewing modes using a user input device;
   determining a recommendation for setting the time window for the selected viewing mode;
   presenting the determined recommendation on the display screen;
   setting the time window for the selected viewing mode using the user input device;
   determining a segment of the ESG signal for presentation according to the selected viewing mode and the time window for the selected viewing mode; and
   presenting the determined segment of the ESG signal on the display screen.

2. The method of claim 1, wherein receiving the data representing the ESG signal comprises receiving data representing an ESG signal sensed during delivery of spinal cord stimulation (SCS).

3. The method of claim 1, wherein the viewing modes further comprise a sample mode for viewing a temporal sample of the ESG signal within a time window for the sample mode.

4. The method of claim 1, further comprising, in response to the metric mode being selected:
   presenting a plurality of parameters determinable from the ECAP portion of the ESG signal on the display screen; and
   receiving a selection of the ECAP parameter from the presented plurality of parameters using the user input device.

5. The method of claim 4, further comprising, in response to the presence mode being selected:

presenting a plurality of features of the ECAP portion of the ESG signal on the display screen; and receiving a selection of a feature for the visualization of the selected feature from the presented plurality of features using the user input device.

6. The method of claim 1, wherein determining the time window for the selected viewing mode comprises:

determining the time window for the metric mode using a timing of delivery of the stimulation pulses and a timing of the ECAP parameter if the metric mode is selected as the viewing mode; and determining the time window for the presence mode using the timing of delivery of the stimulation pulses and a timing of the feature in the ESG signal if the presence mode is selected as the viewing mode.

7. A neurostimulation system for delivering neurostimulation pulses and analyzing responses to the delivery, the system comprising:

a storage device configured to receive and store data representing an electrospinogram (ESG) signal including electrically evoked compound action potentials (ECAPs) evoked by the neurostimulation pulses; and a user interface including:
a display screen;
a user input device; and
a presentation control circuit coupled to the display screen and the user input device, the presentation control circuit configured to:
present on the display screen viewing modes including:
a metric mode for viewing the ESG signal providing for visualization of a signal property indicated by an ECAP parameter determined using an ECAP portion of the ESG signal within a time window for the metric mode, the ECAP portion of the ESG signal including an ECAP of the ECAPs; and
a presence mode for viewing the ESG signal providing for visualization of presence of a feature in the ESG signal within a time window for the presence mode;
receive a selection of the viewing mode from the presented view modes using the user input device;
determine a recommendation for setting the time window for the selected viewing mode;
present the determined recommendation on the display screen;
receive the time window for the selected viewing mode using the user input device;
determine a segment of the ESG signal for presentation according to the selected viewing mode and the time window for the selected viewing mode; and
present the determined segment of the ESG signal on the display screen.

8. The system of claim 7, wherein the presentation control circuit is further configured to receiving a selection of the ECAP parameter for the metric mode from a plurality of ECAP parameters using the user input device, the plurality of ECAP parameters including at least one of:

a peak amplitude being an amplitude of a negative or positive peak of the ECAP in the ECAP portion of the ESG signal;

an area under curve being an area between the ECAP portion of the ESG signal and a baseline for a specified period;

a spectral power related to the ECAP portion of the ESG signal;

a difference between amplitudes of a first negative peak and a second positive peak in the ECAP in the ECAP portion of the ESG signal; and a curve length of the ECAP portion of the ESG signal.

9. The system of claim 7, wherein the presentation control circuit is further configured to present a sample mode of the viewing modes for viewing a temporal sample of the ESG signal within a time window for the sample mode.

10. The method of claim 7, wherein the presentation control circuit is further configured to:

determine the time window for the metric mode using a timing of delivery of the stimulation pulses and a timing of the ECAP parameter if the metric mode is selected as the viewing mode; and determine the time window for the presence mode using the timing of delivery of the stimulation pulses and a timing of the feature in the ESG signal if the presence mode is selected as the viewing mode.

11. The system of claim 7, wherein the presentation control circuit is further configured to, in response to the metric mode being selected:

present a plurality of parameters determinable from the ECAP portion of the ESG signal on the display screen; and receive a selection of the ECAP parameter from the presented plurality of parameters using the user input device; and in response to the presence mode being selected:

present a plurality of features of the ECAP portion of the ESG signal on the display screen; and receive a selection of a feature for the visualization of the selected feature from the presented plurality of features using the user input device.

12. A non-transitory computer-readable storage medium including instructions, which when executed by a system, cause the system to perform a method for delivering neurostimulation pulses and analyzing responses to the delivery, the method comprising:

receiving data representing an electrospinogram (ESG) signal including electrically evoked compound action potentials (ECAPs) evoked by the neurostimulation pulses;

presenting on a display screen viewing modes including:
a metric mode for viewing the ESG signal providing for visualization of a signal property indicated by an ECAP parameter determined using an ECAP portion of the ESG signal within a time window for the metric mode, the ECAP portion of the ESG signal including an ECAP of the ECAPs; and
a presence mode for viewing the ESG signal providing for visualization of presence of a feature in the ESG signal within a time window for the presence mode;

receiving the selection of the viewing mode using a user input device;

determining a recommendation for setting the time window for the selected viewing mode;

presenting the determined recommendation on the display screen;

setting the time window for the selected viewing mode using the user input device;

determining a segment of the ESG signal for presentation according to the selected viewing mode and the time window for the selected viewing mode; and presenting the determined segment of the ESG signal on the display screen.

13. A method for delivering neurostimulation pulses and analyzing responses to the delivery, the method comprising:
receiving data representing an electrospinogram (ESG) signal including electrically evoked compound action potentials (ECAPs) evoked by the neurostimulation pulses;
presenting on a display screen viewing modes including:
a metric mode for viewing the ESG signal providing for visualization of a signal property indicated by an ECAP parameter determined using an ECAP portion of the ESG signal within a time window for the metric mode, the ECAP portion of the ESG signal including an ECAP of the ECAPs; and
a presence mode for viewing the ESG signal providing for visualization of presence of a feature in the ESG signal within a time window for the presence mode;
receiving a selection of a viewing mode from the presented viewing modes using a user input device;
receiving a selection of the ECAP parameter for the metric mode from a plurality of ECAP parameters using the user input device if the metric mode is selected as the viewing mode;
determining a segment of the ESG signal for presentation according to the selected viewing mode and the time window for the selected viewing mode; and
presenting the determined segment of the ESG signal on the display screen,
wherein the plurality of ECAP parameters include at least one of:
a peak amplitude being an amplitude of a negative or positive peak of the ECAP in the ECAP portion of the ESG signal;
an area under curve being an area between the ECAP portion of the ESG signal and a baseline for a specified period;
a difference between amplitudes of a first negative peak and a second positive peak in the ECAP in the ECAP portion of the ESG signal; or
a curve length of the ECAP portion of the ESG signal.

14. The method of claim 13, further comprising measuring the selected ECAP parameter from the ECAP portion of the ESG signal.

15. The method of claim 13, further comprising:
measuring one or more parameters from the ECAP portion of the ESG signal; and
calculating the selected ECAP parameter using the measured one or more parameters.

16. The method of claim 13 wherein the plurality of ECAP parameters comprises at least the peak amplitude.

17. The method of claim 13 wherein the plurality of ECAP parameters comprises at least the area under curve.

18. The method of claim 13 wherein the plurality of ECAP parameters further comprises a spectral power related to the ECAP portion of the ESG signal.

19. The method of claim 13 wherein the plurality of ECAP parameters comprises at least the difference between amplitudes of the first negative peak and the second positive peak in the ECAP in the ECAP portion of the ESG signal.

20. The method of claim 13 wherein the plurality of ECAP parameters comprises at least the curve length of the ECAP portion of the ESG signal.

* * * * *